(12) United States Patent
Whitley et al.

(10) Patent No.: US 7,744,899 B2
(45) Date of Patent: Jun. 29, 2010

(54) RECOMBINANT HERPES SIMPLEX VIRUS USEFUL FOR TREATING NEOPLASTIC DISEASE

(75) Inventors: Richard J. Whitley, Birmingham, AL (US); Bernard Roizman, Chicago, IL (US)

(73) Assignees: The University of Chicago, Chicago, IL (US); UAB Research Foundation, Birmingham, AL (US)

( * ) Notice: Subject to any disclaimer, the term of this patent is extended or adjusted under 35 U.S.C. 154(b) by 183 days.

(21) Appl. No.: 11/546,233

(22) Filed: Oct. 11, 2006

(65) Prior Publication Data

US 2007/0031383 A1 Feb. 8, 2007

Related U.S. Application Data

(63) Continuation of application No. 09/869,674, filed as application No. PCT/US98/27902 on Dec. 31, 1998, now abandoned.

(51) Int. Cl.
*C12N 15/869* (2006.01)
*A61K 48/00* (2006.01)

(52) U.S. Cl. ................. 424/199.1; 514/44 R; 435/320.1

(58) Field of Classification Search .............. 424/199.1; 514/44; 435/320.1
See application file for complete search history.

(56) References Cited

U.S. PATENT DOCUMENTS

| 4,859,587 | A | * | 8/1989 | Roizman | .................. | 424/199.1 |
| 5,231,012 | A | | 7/1993 | Mosmann et al. | | |
| 5,328,688 | A | * | 7/1994 | Roizman | .................. | 424/205.1 |
| 5,328,989 | A | | 7/1994 | Vellekamp et al. | | |
| 5,585,096 | A | | 12/1996 | Martuza et al. | | |
| 5,641,651 | A | * | 6/1997 | Roizman | .................. | 435/69.1 |
| 6,140,114 | A | * | 10/2000 | Klatzmann et al. | ....... | 435/320.1 |
| 6,379,674 | B1 | * | 4/2002 | Rabkin et al. | ............ | 424/199.1 |

FOREIGN PATENT DOCUMENTS

| EP | 0 302 429 B1 | 7/1993 |
| WO | WO 94/14971 | 7/1994 |
| WO | WO 00/40734 | 7/2000 |

OTHER PUBLICATIONS

Andreansky et al. (1998) Gene Therapy, vol. 5, 121-130.*
Vieweg et al. (1994) Cancer Investigation, vol. 13(2), 193-201.*
Orkin et al. (1995), "Report and Recommendations of the Panel to assess the NIH investment in research on gene therapy", 1-20.*
Bronte et al. (1995) J. Immunol. vol. 154, 5283-5292.*
Irvine et al. (1996) J. Immunol., vol. 156, 238 245.*
Vogelstein et al. (1993) Trends in Genetics, vol. 9(4), 138-141.*
Restifo et al (1993) J. Immunother., vol. 14, 182-190.*
Poffenberger et al. (1983) PNAS, vol. 80(9), 2690-2694.*
Advani et al. (Feb. 1998) Gene Therapy vol. 5, 160-165.*

Allione, et al., "Immunizing and Curative Potential of Replicating and Nonreplicating Murine Mammary Adenocarcinoma Cells Engineered with Interleukin (IL)-2, IL-4, IL-6, IL-7, IL-10, Tumor Necrosis Factor *, Granulocyte-Macrophage Colony-stimulating Factor, and *- Interferon Gene or Admixed with Conventional Adjuvants," *Cancer Research* 54:6022-6026 (1994).

Andreansky, et al., "The Application of Genetically Engineered Herpes Simplex Viruses to the Treatment of Experimental Brain Tumors," *Proc. Natl. Acad. Sci. USA* 93:11313-11318 (1996).

Andreansky, et al., "Evaluation of Genetically Engineered Herpes Simplex Viruses as Oncolytic Agents for Human Malignant Brain Tumors," *Cancer Research* 57:1502-1509 (1997).

Andreansky, et al., "Treatment of Intracranial Gliomas in Immunocompetent Mice Using Herpoes Simplex Viruses that Express Murine Interleukins," *Gene Therapy* 5:121-130 (1998).

Aoki, et al., "Expression of Murine Interleukin-7 in a Murine Glioma Cell Line Results in Reduced Tumorigenicity in vivo," *Proc. Natl. Acad. Sci.USA* 89:3850-3854 (1992).

Asher, et al., "Murine Tumor Cells Transduced with the Gene for Tumor Necrosis Factor-*, Evidence for Paracrine Immune Effects of Tumor Necrosis Factor against Tumors," *J. Immunology* 146:3227-3234 (1991).

Ausman, et al., "Studies on the Chemotherapy of Experimental Brain Tumors: Development of an Experimental Model," *Cancer Research* 30:2394-2400 (1970).

Beutler, et al., "Control of Cachectin (Tumor Necrosis Factor) Syntheses: Mechanisms of Endotoxin Resistance," *Science* 232:977-980 (1986).

Blankenstein, et al., "Tumor Suppression after Tumor Cell-targeted Tumor Necrosis Factor * Gene Transfer," *J. Exp. Med.* 173:1047-1052 (1991).

Caruso, et al., "Adenovirus-mediated Interleukin-12 Gene Therapy for Metastatic Colon Carcinoma." *Proc. Natl. Acad. USA* 93:11302-11306 (1996).

Chambers, et al., "Comparison of Genetically Engineered Herpes Simplex Viruses for the Treatment of Brain Tumors in a *Scid* Mouse Model of Human Malignant Glioma," *Proc. Natl. Acad. Sci. USA* 92:1411-1415 (1995).

Cheng, et al., "In vivo Promoter Activity and Transgene Expression in Mammalian Somatic Tissues Evaluated by Using Particle Bombardment," *Proc. Natl. Acad. Sci. USA* 90:4455-4459 (1993).

Cho, et al., "IL-6 Undergoes Transition from in vitro Autocrine Growth Factor to in vivo Growth Inhibitor of B Lymphoma Cells," *J. Biomed. Sci.* 4:201-207 (1997).

Chou, et al., "Mapping of Herpes Simplex Virus-1 Neurovirulence to $*_1 34.5$, a Gene Nonessential for Growth in Culture," *Science* 250:1262-1266 (1990).

Chou, et al., "Differential Response of Human Cells to Deletions and Stop Codons in the $*_1 34.5$ Gene of Herpes Simplex Virus," *J. Virology* 68:8304-8311 (1994).

(Continued)

*Primary Examiner*—Anne Marie S Wehbe
(74) *Attorney, Agent, or Firm*—Marshall, Gerstein & Borun LLP

(57) ABSTRACT

Recombinant herpes simplex viruses comprising DNA encoding cytokines and methods for treating neoplastic diseases using the inventive recombinant viruses are disclosed.

28 Claims, 7 Drawing Sheets

OTHER PUBLICATIONS

Couldwell, et al., "Malignant Glioma Modulation of Immune Function: Relative Contribution of Different Soluble Factors," *J. Neuroimmunol.* 33:89-96 (1991).

Devos, et al., "Molecular Cloning of Human Immune Interferon cDNA and Its Expression in Eukaryotic Cells," *Nucl. Acids Res.* 10:2487-2501 (1982).

Douvdevani, et al., "Reduced Tumorigenicity of Fibrosarcomas which Constitutively Generate IL-1* Either Spontaneously or Following IL-1* Gene Transfer," *Int. J. Cancer* 51:822-830 (1992).

Dranoff, et al., "Activities if Granulocyte-Macrophage Colony-Stimulating Factor Revealed by Gene Transfer and Gene Knockout Studies," *Stem Cells* 12:173-184 (1994).

Fakhrai, et al., "Construction and Characterization of Retroviral Vectors for Interleukin-2 Gene Therapy," *J. Immunother.* 20:437-448 (1997).

Fearon, et al., "Interleukin-2 Production by Tumor Cells Bypasses T Helper Function in the Generation of an Antitumor Response," *Cell* 60 :397-403 (1990).

Finke, et al., "Increase of Proliferation Rate and Enhancement of Antitumor Cytoxicity of Expanded Human CD3$^+$CD56$^+$ Immunologic Effector Cells by Receptor-mediated Transfection with the Interleukin-7 Gene," *Gene Therapy* 5:31-39 (1998).

Golumbeck, et al., "Treatment of Established Renal Cancer by Tumor Cells Engineered to Secrete Interleukin-4," *Science* 254:713-716 (1991).

Goodwin, et al., "Human Interleulcin7: Molecular Cloning and Growth Factor Activity on Human and Murine B-Lineage Cells," *Proc. Natl. Acad. Sci. USA* 86:302-306 (1989).

Gray, et al., "Expression of Human Immune Interferon cDNA in *E. coli* and Monkey Cells," *Nature*, 295:503-508 (1982).

Hock, et al., "Interleukin-7 Induces CD4$^+$ T Cell Dependent Tumor Rejection," *J. Exp. Med.* 174:1291-1298 (1991).

Jenkins, et al., "Herpes Simplex Virus 1 Recombinants with Noninverting Genomes Frozen in Different Isomeric Arrangements are Capable of Independent Replication," *J. Viol.* 59:494-499 (1986).

Krüger-Krasagakes, et al., "Production of Cytokines by Human Melanoma Cells and Melanocyted," *Cancer Research* 139:155-168 (1995).

Lagunoff, et al., "The Regulation of Synthesis and Properties of the Protein Product of Open Reading Frame P of the Herpes Simplex Virus 1 Genome," *J. Virol.* 69:3615-3623 (1995).

Lee, et al., "Isolation and Characterization of a Mouse Interleukin cDNA Clone that Expresses B-Cell Stimulatory Factor 1 Activities and T-cell and Mast-cell-Stimulating Activities," *Proc. Natl. Acad. Sci. USA* 83:2061-2065 (1986).

Lukacs, et al., Transgene-induced Production of IL-4 Alters the Development and COllagen Expression of T Helper Cell 1-type Pulmonary Granulomas, *J. Immunol.* 158:4478-4484 (1997).

Maeda, et al., "Cloning of Interleukin 2 mRNAs From Human Tonsils," *Biochem. Biophys. Res. Com.* 115:1040-1047 (1983).

Maliszewski, et al., "Bovine GM-CSF: Molecular Cloning and Biological Activity of the Recombinant Protein," *Mol. Immunol.* 25:843-850 (1988).

March, et al., "Cloning, Sequence and Expression of Two Distinct Human Interleukin-1 Complementary DNAs," *Nature* 315:641-647 (1985).

Markert, et al., "Reduction and Elimination of Encephalitis in an Experimental Glioma Therapy Model with Attenuated Herpes Simplex Muitants that Retain Susceptibility to Acyclovir," *Neurosurg.* 32:597-603 (1993).

Martuza, et al., "Experimental Therapy of Human Glioma by Means of a Genetically Engineered Virus Mutant," *Science* 252:854-856 (1991).

Moore, et al., "Homology of Cytokine Synthesis Inhibitory Factor (IL-10) to the Epstein-Barr Virus Gene BCRFI," *Science* 248:1230-1234 (1990).

Moore, et al., "Interleukin-10," *Annu. Rev. Immunol.* 11:165-190 (1993).

Moriuchi, et al., "Enhanced Tumor Cell Killing in the Presence of Ganciclovir by Herpes Simplex Virus Type 1 Vector-directed Coexpression of Human Tumor Necrosis Factor-* and Herpes Simplex Virus Thymidine Kinase," *Cancer Research* 58:5731-5737 (1998).

Mulé, et al., "Cellular Mechanisms of the Antitumor Activity of Recombinant IL-6 in Mice," *J. Immunol.* 148:2622-2629 (1992).

Porgador, et al., "Immunotherapy Via Gene Therapy: Comparison of the Effects of Tumor Cells Transduced with the Interleukin-2, Interleukin-6, or Interferon-* Genes," *J. Immunother.* 14:191-201 (1993).

Porgador, et al., "Interleukin 6 Gene Transfection into Lewis Lung Carcinoma Tumor Cells Suppresses the Malignant Phenotype and Confers Immunotherapeutic Competence against Parental Metastatic Cells," *Cancer Research* 52:3679-3686 (1995).

Post, et al., "A Generalized Technique for Deletion of Specific Genes in Large Genomes: * Gene 22 of Herpes Simplex Virus 1 is Not Essential for Growth," *Cell* 25:227-232 (1981).

Ram, et al., "In vivo Transfer of the Human Interleukin-2 Gene: Negative Tumoricidal Results in Experimental Brain Tumors," *J. Neurosurg.* 80:535-540 (1994).

Ram, et al., "Therapy of Malignant Brain Tumors by Intratumoral Implantation of Retroviral Vector-producing Cells," *Nature Medicine* 3:1354-1361 (1997).

Renauld, et al., "Human P40/IL-9: Expression in Activated CD4$^+$T Cells, Genomic Organization, and Comparison with the Mouse Gene," *J. Immunol.* 144:4235-4241 (1990).

Restifo, et al., "Identification of Human Cancers Deficient in Antigen Processing," *J. Exp. Med.* 177:265-272 (1993).

Richter, et al., "Interleukin 10 Transfected into Chinese Hamster Ovary Cells Prevents Tumor Growth and Macrophage Infiltration," *Cancer Research* 53:4131-4137 (1993).

Rinderknecht, et al., "Natural Human Interferon-*. Complete Amino Acid Sequence Determination of Sites of Glycosylation," *Biol. Chem.* 259:6790-6797 (1984).

Roizman, et al., "Genetic Engineering of Novel Genomes of Large DNA Viruses," *Science* 229:1208-1218 (1985).

Roszman, et al., "Modulation of T-Cell Function by Gliomas," *Immunology Today* 12:370-374 (1991).

Schumacher, et al., "Use of Clinically Relevant Human-*scid*-mouse Models in Metastasis Research," *TIBTECH* 15:239-241(1997).

Shih, et al., "Expression of Hepatitis B Virus *S* Gene by Herpes Simplex Virus Type 1 Vectors Carrying *- and *- Regulated Gene Chimeras," *Proc. Natl. Acad. Sci. USA* 81:5867-5870 (1984).

Souza, et al., "Recombinant Human Granulocyte Colony-Stimulating Factor: Effects on Normal and Leukemic Myeloid Cells," *Science* 232:60-65 (1986).

Tada, et al., "Cellular and Cytokine Responses of the Human Central Nervous System to Intracranial Administration of Tumor Necrosis Factor * for the Treatment of Malignant Gliomas," *Cancer Immunol. Immunother.* 36:251-259 (1993).

Taniguchi, et al., "Structure and Expression of a Cloned cDNA for Human Interleukin-2," *Nature* 302:305-310 (1983).

Takamiya, et al., "Gene Therapy of Malignant Brain Tumors: A Rat GLioma Line Bearing the Herpes Simplex Virus Type 1-Thymidine Kinase Gene and Wild Type Retrovirus Kills other Tumor Cells," *J. Neurosci. Res.* 33:493-503 (1992).

Tepper, et al., "Review: Experimental and Clinical Studies of Cytokine Gene-Modified Tumor Cells," *Human Gene Therapy* 5:153-164 (1994).

Tjuvajev, et al., "RG-2 Glioma Growth Attenuation and Severe Brain Edems Caused by Local Production of Interleukin-2 and Interferon-*," *Cancer Research* 55:1902-1910 (1995).

VanCott, et al., "Regulation of Mucosal and Systemic Antibody Responses by T Helper Cell Subsets, Macrophages, and Derived Cytokines Following Oral Immunization with Live Recombinant *Salmonella*," *J. Immunology* 156:1504-1514 (1996).

Vieira, et al., "Isolation and Expression of Human Cytokine Synthesis Inhibitory Factor cDNA Clones: Homology to Epstein-Barr Virus Open Reading Frame BCRFI," *Proc. Natl. Acad. Sci. USA* 88:1172-1176 (1991).

Vigon, et al., "Molecular Cloning and Characterization of *MPL*, the Human Homolog of the V-*mpl* Oncogene: Identification of a Member of the Hematopoietic Growth Factor Receptor Superfamily," *Proc. Natl. Acad. Sci. USA* 89:5640-5644 (1992).

Wei, et al., "Enhancement of Interleukin-4-Mediated Tumor Regression in Athymic Mice by In Situ Retroviral Gene Transfer," *Human Gene Therapy* 6:437-443 (1995).

Wiranowska, et al., "Evaluation of Blood-brain Barrier Permeability and the Effect of Interferon in Mouse Glioma Model," *J. Neuro-Oncology* 14:225-236 (1992).

Yu, et al., "Treatment of Glioma by Engineered Interleukin 4-Secreting Cells," *Cancer Research* 53:3125-3128 (1993).

Supplementary European Search Report in EP 98 966 139.2 dated Jul. 30, 2002.

Bennett et al., "Interleukin 12 Secretion Enhances Antitumor Efficacy of Oncolytic Herepes Simplex Viral Therapy for Colorectal Cancer," *Ann. Surg.*, 233:819-826, (2001).

Jarnagin, et al., "Neoadjuvant Treatment of Hepatic Malignancy: an Oncloytic Heropes Simplex Virus Expressing IL-12 Effectively Treats the Parent Tumor and Protects Against Recurrence-After Resection," *Cancer Gene Ther.*, 10:215-223, (2003).

Meignier, "Genetically Engineered Attenuated Herpes Simplex Viruses," *Rev. Infect. Dis.*, 13:S895-S897 (1991).

Varghese et al., "Systemic Oncolytic Herpes Virus Therapy of Poorly Immunogenic Prostate Cancer Metastatic to Lung," *Clin. Cancer Res.*, 12:2919-2927, (2006).

Wong, et al., "Cytokine Gene Transfer Enhances Herpes Oncolytic Therapy in Murine Squamous Cell Carcinoma," *Human Gene Ther.*, 12:253-265 (2001).

Wong, et al., "Effective Intravenous Therapy of Murine Pulmonary Metastases with an Oncolytic Herpes Virus Expressing Interleukin 12," *Clin. Cancer Res.*, 10:251-259, (2004).

* cited by examiner

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 43 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

GTAACCCTCG AGGGTACCAG ATCTGTCGAC GATATCTCTA GAT      43

(2) INFORMATION FOR SEQ ID NO: 2:

(i) SEQUENCE CHARACTERISTICS:
      (A) LENGTH: 42 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 2:

CCGGATCTAG AGATATCGTC GACAAGTCTG GTACCCTCGA GG    42

RECOMBINANT HERPES SIMPLEX VIRUS USEFUL FOR TREATING NEOPLASTIC DISEASE

U.S. GOVERNMENT RIGHTS

The U.S. government may own certain rights in the invention pursuant to grants from the National Institutes of Health (NC1-CA47451, NIAID-AI124009, NC1-K12-CA01719, and NINDS-NS31096) and a research grant from the U.S. Department of Energy (DEFG05-93ER61654).

BACKGROUND OF THE INVENTION

1. Field of the Invention

The invention generally relates to methods for the treatment of cancer and other neoplastic diseases and, more specifically, to recombinant herpesviruses comprising DNA encoding various cytokines and their use in treating cancer and other neoplastic diseases of the central nervous system.

2. Related Technology

Neoplastic diseases of the central nervous system (CNS) present a tremendous therapeutic challenge in spite of advances in accepted treatment modalities such as surgery, radiotherapy, and chemotherapy. Survival of patients afflicted with certain types of brain tumors from the time of diagnosis is usually measured in months, while recurrence after treatment is normally associated with a life expectancy measured in weeks. More recent therapies involve the use of genetically engineered viruses and immunotherapy to destroy tumor cells.

Genetically engineered (recombinant) viruses have been studied at length for use as vectors for achieving a number of therapeutic objectives. Such objectives include (1) delivery to cells of normal copies of genes to circumvent the pathologic effect of missing or mutated endogenous genes, 2) selective destruction of cancer cells, and 3) immunization with one or more antigens in order to confer immunity to an infectious agent or to stimulate the host's immune system function so as to recognize, for example, tumor associated antigens.

Approaches to viral therapy of neoplastic disease are twofold. A first approach includes the use of non-destructive viruses (e.g. genetically-altered retroviruses) to introduce into cells genes that express an enzyme such as the herpes simplex virus (HSV) thymidine kinase enzyme that the cells do not otherwise express. The rationale of this type of therapy is to selectively provide tumor cells with an enzymatic activity that is lacking or is much lower in the normal cells and which renders the tumor cells sensitive to certain drugs. For example, drugs such as gancyclovir and acyclovir require phosphorylation by thymidine kinase before they are active. Providing tumor cells with the viral thymidine kinase gene allows the cells to phosphorylate and thus activate the drug which may then be incorporated into the DNA of dividing tumor cells or otherwise inhibit DNA synthesis in those cells, thereby leading to the destruction of the cells.

Another approach to viral therapy of neoplastic disease involves direct inoculation of tumor with debilitated or attenuated viruses, which require for replication, certain factors that are present in tumor cells but that are not present in normal cells. For example, tk⁻ HSV mutants (i.e., HSV mutants lacking the tk or thymidine kinase gene) have been directly injected into tumors in mice having CNS neoplastic disease, thereby leading to the infection and ultimate destruction of the tumor cells. Nonetheless, some of the test animals died presumably of viral encephalitis before any tumor-related deaths in the control group. [Martuza et al., *Science* 252:854-856 (1991)]

The rationale for the use of tk⁻ viruses is based on the fact that such mutant viruses are totally dependent on cellular thymidylate synthetase as a source of thymidine triphosphate for DNA replication. Therefore, these mutant viruses exhibit a reduced virulence for normal central nervous system tissues yet are able to actively multiply in and infect tumor cells which have sufficient levels of thymidylate synthetase to support viral DNA synthesis thereby causing the destruction of the tumor cells.

In practice, a number of limitations to this approach to viral therapy of neoplastic disease exist. Specifically, a major limitation to the use of tk⁻ viruses is that these mutant viruses are not completely avirulent. Another limitation to this approach is the lack of a secondary or alternative mechanism of action. More particularly, in the event complications arise to compromise the primary mechanism of action (i.e., infection and destruction of tumor cells), unlike the tk⁺ viruses discussed above, the tk⁻ viruses would be unable to phosphorylate such pro-drugs as acyclovir or gancyclovir to an active form (due to the lack of thymidine kinase), thereby not providing or alternative or a secondary mechanism of action.

An alternative to the viral mutants referenced to above is the use of HSV mutants (in which a particular gene or genes are rendered incapable of producing an active gene product) that are unable to grow in the normal CNS cells but which are capable of growth in CNS tumor cells. One such gene is the $\gamma_1 34.5$ gene. The $\gamma_1 34.5$ gene maps within the inverted repeats ab and b'a' sequences flanking the unique long ($U_L$) domain of the HSV genome and is, therefore, present in two copies per genome. [Chou et al., *Science,* 250:1262-1266 (1990).]

Numerous studies have been conducted with HSVs in which the $\gamma_1 34.5$ gene or genes have been inactivated by substitutions, deletions, or insertions of mutations. For example, it has been shown that $\gamma_1 34.5$ (null) mutants are highly attenuated (PFU/$LD_{50}$ratios>$10^6$) in mice. Further, it has been demonstrated that in cells of human derivation infected with $\gamma_1 34.5^-$ viruses, initiation of viral DNA synthesis induces a total shutoff of protein synthesis and results in reduced viral yields.

Studies using the $\gamma_1 34.5$ deletion mutant (R3616) for the therapy of central nervous system tumors indicate that this virus is superior to deletion mutants used previously. More particularly, it was shown that a $\gamma_1 34.5^-$ virus (i.e., the R4009 virus, containing a mutation via insertion of an in-frame stop codon in the $\gamma_1 34.5$ genes), is significantly better than the R3616 null mutant in its ability to destroy cancer cells and prolong the life of mice bearing central nervous tumors. In some instances, mice survived tumor free.

The use of genetically engineered herpes simplex virus (HSV) for treatment of malignant gliomas has been described previously. As these studies used immunocompromised mice, a central question arose as to (1) whether the infection induced an immune response to the tumor cells, and (2) whether the response could be modified by cytokines expressed from genes cloned into the virus.

Enhancement of the immune response to malignant gliomas has recently emerged as a major avenue of potential therapy. This approach is based on the observation that patients with malignant brain tumors are immunosuppressed (i.e., immunosuppression of T-cell functions). Although gliomas are poor antigen-presenting cells in vivo with low expression of MHC class I and II antigens, they also secrete several glioma suppressor factors such as TGF-β2 and prostaglandin $E_2$. Therefore, a major goal of cancer immunotherapy is to stimulate recognition of tumor cells by the host's immune system and to activate tumor antigen-specific cellular immunity.

Direct transfer of cytokine genes in tumor cells has emerged as a powerful immunotherapeutic tool in the new approaches for the management of cancer patients. In experiments with animal models, tumor cells transduced with cytokine or growth factor genes such as interleukin IL-1, IL-2, IL-4, IL-6, IL-7, interferon (IFN-γ), tumor necrosis factor (TNF)-α, and granulocyte-macrophage colony stimulating factor (GM-CSF) have demonstrated in vivo inhibition of tumor growth by stimulating localized inflammatory and/or immune responses. In contrast, cytokines like IL-5 and IL-10 fail to stimulate host immunity and do not kill tumor cells. Transforming growth factor β2 (TGF-β2) has been shown to decrease or inhibit immunogenicity.

The therapeutic efficacy of cytokine therapy in intracerebral neoplastic disease has been tested only recently. More specifically, retrovirus vectors have been utilized primarily to transduce cytokine genes into glioma cells. Initial results from these studies have been mixed, at best. Therefore, there remains a need for a more suitable viral vector with which to introduce therapeutic genes, e.g., cytokine genes, into central nervous system tumors, for the purpose of treating the neoplastic disease. Preferably, such viral vectors (i.e., adenovirus, adeno-associated virus and herpes simplex virus or others) are capable of expressing the foreign gene (i.e., cytokine) and/or are capable of replicating conditionally within the tumor area. A further desirable characteristic would be that the viral vector be highly neurotropic. Such characteristics are expected to produce a more potent cytokine-mediated anti-tumor effect as compared to the cytokine-mediated anti-tumor effect obtained via administration of a retroviral vector.

SUMMARY OF THE INVENTION

The invention is directed to recombinant herpes simplex viruses incapable of expressing an active $\gamma_1 34.5$ gene product and comprising DNA encoding a cytokine. Also provided are herpes simplex virus DNAs incapable of expressing an active $\gamma_1 34.5$ gene product and further comprising a DNA encoding a cytokine.

The invention is also directed to host cells transformed or transfected by the recombinant herpes simplex virus or the DNAs of the invention.

Further, the invention is directed to methods of treating neoplastic diseases, especially neoplastic diseases of the central nervous system via administration of the recombinant herpes simplex viruses or the herpes simplex virus DNAs of the invention to patients having a neoplastic disease.

Other objectives and advantages of the invention may be apparent to those skilled in the art for a review of the following detailed description, including the drawings, and the approved claims.

DETAILED DESCRIPTION OF THE INVENTION

Figure 1:
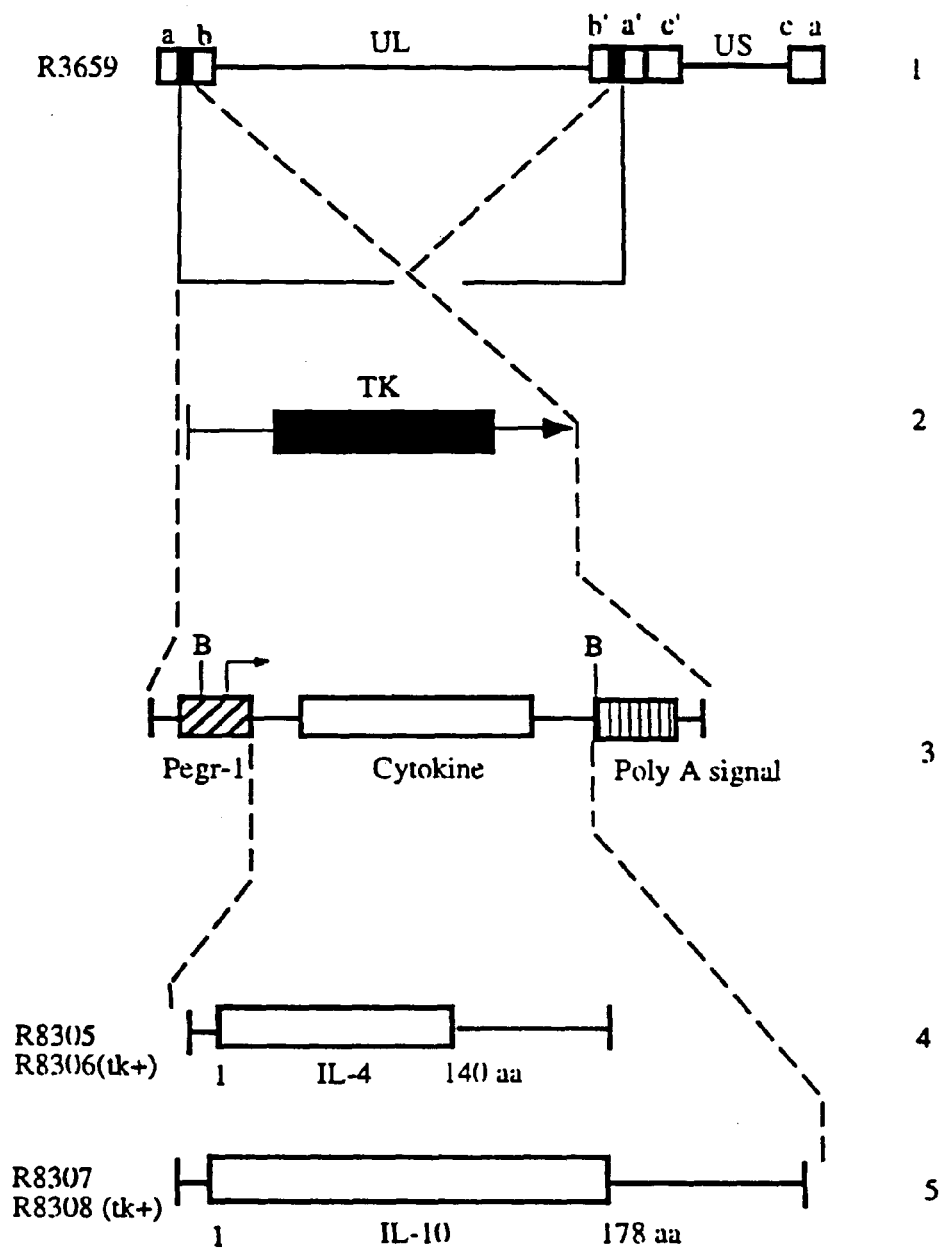
FIG. 1 depicts a structure of a cytokine expressing viruses as schematic representations of sequence arrangements of recombinant virus R3659 and the mutant viruses derived therefrom. Line 1: the genomic structure of recombinant virus R3659, constructed from HSV-1(F) Δ305, lacks the StuI-BstEII fragment from domain of $\gamma_1 34.5$ gene, which is replaced by the chimeric α27-tk gene. Line 2: the filled bar indicates the coding domain of the tk gene, and the thin line on the left side (5') indicates the α27 promoter. The arrow indicates the direction of transcription. Line 3: the cytokine cloning cassette. The open bar indicates the position of the cytokine cloned into the cassette, the diagonal hatched bar on the left side (5') indicates the Egr-1 promoter sequence. The vertical hatched bar on the right side (3') indicates the hepatitis B virus poly-A signal sequence. The arrow indicates the site of transcription initiation. "B" represents the BamHI restriction site. Lines 4 and 5: sequence arrangements of recombinant viruses R8305/R8306(tk$^+$) and R8307/R8308 (tk$^+$). The open bars indicate the coding sequences of murine IL-4 or IL-10 cDNA. The thin lines represent the untranslated region of murine IL-4 or IL-10 cDNA.

The treatment of human neoplastic diseases of the central nervous system remains a formidable problem inasmuch as therapeutic advances have not significantly improved clinical outcome. The utilization of viruses to treat such diseases is one of the current therapeutic modalities under intensive study as possible therapeutic agents in humans. Current studies have been built upon prior observations which recognize that a recombinant HSV that is incapable of producing an active $\gamma_1 34.5$ gene product significantly prolonged survival, and in some instances cured scid mice implanted intracerebrally with human glioma cells.

A central problem in the treatment of neoplastic diseases of the central nervous with oncolytic viruses rests on the fact that it is unlikely that all tumor cells can be infected and destroyed by a single or even multiple administrations of the virus. Hence effective treatment should take into account other factors such as host immune response in addition to the cytotoxic effects resulting from viral gene expression.

In order to address this problem, recombinant herpes simplex viruses are provided which are capable of preferentially killing neoplastic CNS cells instead of normal CNS cells, and which provide a further means for modulating the host's immune response so as to augment the therapeutic effectiveness of the recombinant viruses. This first prong of this two-pronged therapeutic effect is achieved by providing a herpes simplex virus having genomic alterations which render the virus capable of preferentially killing tumor cells instead of normal cells. This is achieved (by way of non-limiting example) by provided a herpes simplex virus incapable of expressing an active $\gamma_1 34.5$ gene product. Such viruses may lack $\gamma_1 34.5$ genes altogether or may have altered $\gamma_1 34.5$ genes which do not permit expression of an active gene product. The $\gamma_1 34.5$ gene alterations may include nucleotide substitutions which result in a gene product having an altered amino acid composition which renders the gene product inactive. Other alterations include the insertion of stop codons, deletions of portions of the gene and alterations in promoter/regulatory regions of the gene which prevent expression of the $\gamma_1 134.5$ genes. Chou et al., *Science*, 250:1262-1266 (1990). Other viral genomic alterations such as the insertion of DNA into the $\gamma_1 34.5$ genes which, when expressed, do not produce an active $\gamma_1 34.5$ gene product are also contemplated. Still other genomic alterations encompassed by the invention involve the inactivation of genes whose expression product activates or induces expression of $\gamma_1 34.5$ genes. Other genomic alterations may facilitate selection of recombinant viruses or may confer altered growth properties on the virus. Methods for preparing such recombinant viruses are well known in the art and such methods are exemplified below. Also encompassed by the invention are viruses which express only one copy of the $\gamma_1 34.5$ genes.

The second prong of the therapeutic effect achievable by use of the present invention involves providing to the tumor-bearing host, a means for modulating its immune response so as to more effectively recruit components of the host immune system to the tumor site and/or to stimulate a hormonal response and, as a result, to augment tumor cell killing. Accordingly, a recombinant herpes simplex virus incapable of expressing an active $\gamma_1 34.5$ product is further modified so as to comprise an expressible DNA (for example a cDNA) encoding a cytokine. The cytokine-encoding DNA comprising the viruses of the present invention may be under the regulatory control of a herpesvirus promoter or an exogenous promoter capable of directing expression of the cytokine-encoding DNA during the infection cycle of the recombinant virus. The promoters may be derived from the group of promoters consisting of herpes simplex virus immediate early, early, and late promoters, or they may be hybrid promoters which permit prolonged expression of the cytokine-encoding DNA during the replication cycle of the virus. In a preferred embodiment of the invention, the cytokine-encoding DNA is under the promoter-regulatory control of the HSV EGR-1 promoter. Synthetic promoters useful in the practice of the invention are exemplified by a promoter comprising a herpes simplex virus $\alpha$ gene promoter fragment operatively linked 5' to a herpes simplex virus $\gamma$ gene promoter fragment since, as those described in U.S. Pat. No. 5,641,651, the disclosure of which is incorporated herein by reference. An illustrative synthetic promoter comprises a herpes simplex virus $\alpha$ gene promoter fragment operatively linked 5' to a herpes simplex virus $\gamma$ gene promoter fragment. The a gene fragment may comprise promoter sequences upstream of the transcription initiation site of the $\alpha 4$ gene and the $\gamma$ gene promoter fragment may comprise a transcription initiation site and the 5' non-coding region of the $\gamma_1 U_L 19$ gene.

The cytokine-encoding DNA may be inserted at any location in the herpesvirus genome so long as the insertion does not disrupt a region of the viral DNA necessary to its tumor cell cytolytic functions, and so long as the DNA can be expressed to produce a cytokine.

A preferred site for insertion of the cytokine-encoding DNA is in $\gamma_1 34.5$ gene or a region of the HSV genome from which the $\gamma_1 34.5$ genes were deleted.

Recombinant viruses of the invention may also comprise more than one copy of a cytokine DNA or may comprise two or more different cytokine-encoding DNAs so as to optimize the immunostimulatory effects of the virus.

Among the cytokines contemplated for use in the invention are IL-1, IL-2, IL-4, IL-5, IL-6, IL-7, IL-10, interferon (IFN-$\gamma$), and tumor necrosis factor (TNF-$\alpha$), all of which have demonstrated in vivo inhibition of tumor cell growth by at least in part, stimulating localized inflammatory and/or immune responses.

A number of cytokine encoding DNAs which are useful in the practice of the present invention are described in the following references which are incorporated herein by reference. For example, Douvdevani et al. describe an IL-1 encoding DNA which, when transferred into fibrosarcoma cells, reduces their tumorigenicity. March et al., *Nature*, 315:641 (1985) have described an IL-1 encoding DNA useful in the practice of the present invention. DNAs encoding IL-2 and which are useful in the practice of the present invention have been described by Taniguchi et al., *Nature*, 302:305 (1983), Maeda et al., *Biochem. Biophys. Res. Commun.*, 115:1040 (1983), and Fearon et al., *Cell*, 60:397-403 (1990). Il-4 encoding DNA which is useful in the practice of the present invention has been described by Yakota et al., *Proc. Natl. Acad. Sci., USA*, 83:2061-2065 (1986) American Type Culture Collection (ATCC) 10801 University Blvd., Manassas, Va. 20140-2209 (ATCC Accession No. 32561) and Golumbeck et al., *Science*, 254:713-716 (1991). IL-6 encoding DNA has been described by Porgador et al., *Cancer Res.*, 52:3679-3686. DNA encoding IL-7 has been described by Goodwin et al., *Proc. Natl. Acad. Sci., USA*, 86:302 (1989).

Interferon gamma (IFN $\gamma$) encoding cDNAs have been described by Gray et al., *Nature*, 295:503 (1982); Devos et al., *Nucl. Acids Res.*, 10(8):2487 (1982); Rinderknecht, E., *J. Biol. Chem.*, 259(11):6790 (1984); and ATCC Accession No.

185990. As is readily apparent, cytokine encoding DNAs according to the invention may be of human or non-human origin.

Methods for inserting cytokines encoding DNAs such as those described above into the viral genome are well known in the art and are described, for example, in *Current Protocols in Molecular Biology*, Ausubel et al., Eds. John Wiley and Sons USA (1997) (incorporated herein by reference) and are exemplified in detail below. Methods for obtaining cytokine-encoding DNA from various species, including humans, are well known in the art and depends primarily on the ability of the cytokine-encoding DNA to hybridize across species. Such methods are described in detail in *Current Protocols in Molecular Biology*, supra (incorporated herein by reference) Polymerase chain restriction methods may also be used to obtain cytokine-encoding DNAs from a variety of species (including human). See, e.g., *Current Protocols in Molecular Biology*, supra (incorporated herein by reference).

By way of illustration, in one embodiment of the present invention, a recombinant herpes simplex virus type I was prepared in which both copies of the viral $\gamma_1 34.5$ genes were replaced by chimeric IL-4-encoding DNAs. The construction of the recombinant virus was accomplished by a two-step process. In the first step, HSV-1 genome was modified by replacing its $\gamma_1 134.5$ genes with a chimeric gene consisting of the coding domain of an HSV-1 thymidine kinase (tk) gene fused to a promoter derived from the $\alpha 27$-tk genes with a chimeric murine IL-4 gene under the regulatory control of an EGR-1 promoter and which further comprises a hepatitis B virus polyadenylation signal. Another recombinant HSV-1 was similarly prepared wherein the viral $\gamma_1 34.5$ genes were replaced with a cDNA encoding murine IL-10 which was also placed under the regulatory control of an EGR-1 promoter and which further comprises a hepatitis B mix polyadenylation signal.

Another therapeutic approach according to the invention involves the use of two or more recombinant herpes simplex viruses which express different cytokines which may have additive or synergistic effects on the host's immune system.

The recombinant viruses of the invention may be administered to the tumor-bearing host by any of a number of approaches well known to those of skill in the art. Direct intratumoral injection provides a controllable means of treating tumors. Retrograde axonal transport is another means by which the recombinant viruses may be introduced into a tumor, from a site remote from the tumor.

The invention is also directed to methods of using the recombinant viruses of the present invention for the treatment of tumors and pharmaceutical compositions comprising a recombinant virus of the invention in a pharmaceutically acceptable diluent, adjuvant, or carrier. The methods include treatment of the tumors with one or more of the viruses of the present invention as well as combination therapies by which the tumor-bearing patient is treated with other therapeutic modulates such as radiation, chemotherapy, or surgery along with or as an adjunct to treatment with the recombinant viruses.

While a variety of cytokines were available, interleukin-4 (IL-4) and interleukin-10 (IL-10) were chosen for initial studies. However, other cytokines. The selection of IL-4 was predicated upon its known ability to induce macrophage and CD8 T cell proliferation as well as B lymphocyte differentiation. IL-4 is also one of the few interleukins whose interaction with its receptors is species-specific. To contrast with this potential for enhancement of the immune response, IL-10 was selected because of its known capacity to suppress host immune responses. The expectation was that if the cytokines were not expressed or if the immune system played little or no role in tumor progression, the median survival of tumor-bearing mice treated with cytokine-expressing virus would be similar to that of mice treated with non-cytokine-expressing virus.

Immunocompetent C57BL/6 mice with intracranial gliomas induced with syngeneic GL-261 cells were utilized to assess the effects of recombinant $\gamma_1 34.5^-$ viruses comprising DNA encoding cytokines on the gliomas.

The invention is illustrated by the following examples, which are not intended to limit the scope of the invention as recited in the claims.

Example 1 provides the methods for construction of exemplary recombinant herpesviruses of the invention.

Example 2 describes a comparison of the replication competence of recombinant HSVs (R8306 and R8308) and wild-type HSV (HSV-1[F]) in both Vero cells and human foreskin fibroblasts.

Example 3 describes the ability of the wild-type (HSV-1 [F]) and recombinant HSVs (R8306 and R8308) to replicate in tumor (glioma) cell lines U251MG and D54MG.

Example 4 illustrates the production of cytokines IL-4 and IL-10 by Vero cells infected by recombinantly-produced HSVs that contain DNA encoding murine IL-4 or IL-10.

Example 5 describes (a) the sensitivity of tumor cells to the direct cytolytic effects of HSVs R8306 and R8308, (b) the relation between the quantity of GL-261 glioma cells injected intracerebrally and host survival, and (c) the sensitivity of in vivo tumors to the treatment of either HSV R8306 or HSV R8308.

Example 6 describes the infiltration of immune-related cells (i.e., macrophages, CD4+ and CD8+ T cells) into tumor sites treated with recombinantly produced HSVs containing DNA encoding murine interleukins.

Example 1

Construction of Recombinant HSV Containing DNA Encoding Murine IL-40R IL-10

While the following is exemplified by the use of herpes simplex type 1 (HSV-1), other herpesviruses, whose genomic structures have been characterized such as HSV-2, may be also employed in the practice of the present invention.

Recombinant viruses (HSV) were constructed in which both copies of the $\gamma_1 34.5$ gene in the wild type HSV-1(F) were replaced by cDNAs encoding specific cytokines (i.e., the HSVs lacked expressible $\gamma_1 34.5$ genes). Specifically, the cDNAs of the inserted cytokines either encoded 140 codons for interleukin-4 (IL-4) or 178 codons for interleukin-10 (IL-10). HSV-1(F) is a low passage clinical isolate used as the prototype HSV-1 strain and has been described in detail previously [Post et al., *Cell* 25:227-232 (1981) and Jenkins et al., *J. Virol.* 59:494-499 (1986), both incorporated herein by reference].

The construction of the recombinant viruses was performed via a two step process. In the first step, the $\gamma_1 34.5$ genes were replaced by a chimeric gene consisting of the coding domain of the HSV-1 (F) tk gene fused to the promoter of the $\alpha 27$ HSV gene to yield a recombinant virus R3659 described previously [Lagunoff and Roizman, *J. Virol.* 69:3615-3623 (1995), incorporated herein by reference)]. In the second step, both copies of the $\alpha 27$-tk genes were replaced by the chimeric genes encoding the cytokines as described directly below.

Plasmids

Plasmids containing murine cytokines were obtained from the American Type Culture Collection (Manassas, Va.). Plasmid p2A-E3 (ATCC accession no. 37561) contained a 0.59 kbp BamHI fragment of murine IL-4 encoding cDNA cloned into the BamHI site of pBR322. Plasmid pcD(SRalpha)-F15 contained a 1.34 kbp fragment of murine cDNA encoding IL-10 cloned into the BamHI site of pBR322. The plasmid pRB4874 contained a 0.48 kbp XbaI-SalI fragment of the Egr-1 promoter sequences. The pRB4875 contained the BamHI S fragment of HSV-1(F) cloned into the BamHI site of pUC19. The pRB3879 contained a 0.58 kbp DNA fragment encoding the hepatitis B virus polyA signal sequences.

To construct a cytokine expressing cassette, pRB4875 was cleaved with SbtEII and BspEI, and a 0.77 kbp fragment containing most of the $\gamma_1 34.5$ gene coding sequences was replaced with the double stranded DNA oligomer linker

```
                                        (SEQ ID NO. 1)
    GTAACCCTCGAGGGTACCAGATCTGTCGACGATATCTCTAGAT
``` and its complement,

```
                                        (SEQ ID NO. 2)
    CCGGATCTAGAGATATCGTCGACAAGTCTGGTACCCTCGAGG
``` to yield pRB4876. pRB4876 was then digested with XhoI and then treated with Klenow fragment to blunt the ends of the DNA fragments. A 0.48 kbp SphI-KpnI fragment containing the Egr-1 promoter from pRB4874 was blunt-ended with T4 polymerase and ligated in the XhoI/Klenow site of pRB4876, yielding plasmid pRB4877. Plasmid pRB4877 was digested with EcoRI and a 0.58 kbp KpnI fragment containing hepatitis B polyA signal sequence from pRB3879 was blunt-ended with T4 polymerase and then inserted into the EcoRV site of pRB4877, resulting in plasmid pRB4878 that consists of the Egr-1 promoter, polylinker sites and the hepatitis B polyadenylation signal.

To construct the cytokine expressing plasmid pRB4879, plasmid pRB4878 was cleaved with KpnI and blunt-ended with T4 polymerase, then a 0.95 kbp BamHI-HindIII/Klenow fragment containing IL-10 cDNA from pcD(Sralpha)-F15 was then inserted into the blunt ended KpnI site of pRB4878. In this plasmid, the expression of IL-10 was driven by the Egr-1 promoter. Plasmid pRB4881 was constructed by ligating a 0.59 kbp BamHI/Klenow fragment that contained IL-4 cDNA from p2A-E3 into the blunt ended KpnI site of plasmid pRB4878.

Construction of Recombinant Viruses

Transfection of viral DNA was performed in rabbit skin cells by a method previously described in Post et al., *Cell*, 25:227-232 (1981) and in U.S. Pat. No. 5,328,688, both of which are incorporated herein by reference. Selection for recombinant viruses that were tk$^+$ was performed on human 143TK$^-$ (thymidine kinase minus) cells (cells obtained from Dr. Carlo Croce, Thomas Jefferson University, School of Medicine, Philadelphia Pa. although other TK$^-$ cells may be used for the selection overlaid in HAT medium (Dulbecco's Modified Eagle Medium) containing 5% fetal bovine serum, hypoxanthine, aminopterin and thymidine), whereas the selection of tk$^-$ viruses was accomplished via the use of human 143TK$^-$ cells overlaid with Dulbecco's Modified Eagle Medium containing 5% newborn calf serum and 100 µg of bromodeoxyuridine (BUdR) per ml of medium. See, Post et al., *Cell*, 25:227-232 (1981) and U.S. Pat. No. 5,328,688 incorporated herein by reference. Viral DNAs were isolated from infected cells and purified on NaI gradients using the method described by Roizman et al., *Science* 129:1208-1218 (1985), incorporated herein by reference. The recombinant viruses R8305 and R8307 were obtained by co-transfection of R3659 [Chou et al., *J. Virol* 68:8304-8311 (1994), incorporated herein by reference] viral DNA with either plasmid pRB4881 or pRB4879 and by selecting tk$^-$ progeny viruses in human 143TK$^-$ cells overlaid with medium containing BUdR. Recombinant viruses R8306 and R8308 were constructed by co-transfection of rabbit skin cells with R8305 or R8307 viral DNA, respectively with plasmid pRB4867. tk$^+$ viruses corresponding to R8306 and R8308 were selected by plating the progeny of transfection on 143TK$^-$ cells in HAT medium. The genotype of recombinant viruses selected in this fashion was verified by hybridization of electrophoretically separated restriction enzyme digests with appropriate 32[p] labeled DNA probes as previously described [Shih et al., *Proc. Natl. Acad. Sci.* 81:5867-5870 (1984), incorporated herein by reference]. FIG. 1 sets forth a schematic illustration of the structure of these wild type and recombinant viruses.

The following recombinant viruses which lack a $\gamma_1 34.5$ gene capable of expressing an active gene product and which further comprise the indicated cytokine-encoding DNA and which are preferred embodiments of the present invention were deposited with the American Type Culture Collection, 10801 University Boulevard, Manassas, Va. 20110 on Jul. 1, 1998, and have been assigned the following accession nos.:

| Virus | Accession No. |
|---|---|
| R8306 (IL-4) | VR-2622 |
| R8308 (IL-10) | VR-2621 |
| R8314 (IL-2) | VR-2623 |
| R8316 (IL-5) | VR-2620 |

Example 2

Replication of Wild-Type and Recombinant HSV In Vero and Human Foreskin Fibroblasts Earlier studies have shown that $\gamma_1 34.5^-$ viruses replicate efficiently in Vero cells. Therefore, replication competence comparison studies of the recombinant virus (R8306 IL4 or R8308 IL10) and wild-type HSV [HSV-1(F)] were undertaken in Vero cells (obtained from American Type Culture Collection, Rockville, Md.). Comparison replication competence studies were also conducted in human foreskin fibroblasts. The ability of the engineered HSV recombinants to replicate in Vero and human foreskin fibroblasts was determined by infecting cells at a multiplicity of infection (MOI) of 0.1 plaque forming units/cell (PFU/cell)

Dividing and contact-inhibited cultures of Vero and human foreskin fibroblasts were generated as follows. Two sets of trypsinized cells were plated in 24-well tissue culture trays (Becton-Dickinson, Rutherford, N.J.). One set of cells was infected with either the recombinant viruses or HSV-1 (F) 24 hrs post-seeding (dividing subconfluent cells). The second set was incubated for three days in medium containing 7% fetal bovine serum and subsequently transferred into medium containing 2% fetal bovine serum for an additional two days to generate contact inhibited monolayers prior to infection with either the recombinant viruses or HSV-1(F) (confluent comparison). Infected vero cell monolayers were harvested at 24 and 48 hours post-infection and sonicated. Resulting lysates were assayed for their ability to form plaques on Vero cell monolayers. Vero cells were fixed and stained with May-Grünwald (Aldrich Chemical Company, Milwaukee, Wis.) and Giemsa (Sigma Diagnostics, St, Louis, Mo.) stains and plaques were counted by light microscopy. Results shown in Table 1 (below) indicate no significant differences in the ability of wild-type or recombinant viruses to replicate in either confluent or subconfluent Vero cultures.

TABLE 1

Replication of Wild-Type and Recombinant Viruses
In Subconfluent and Confluent Vero Cell Cultures
(data express as plaque-forming units (PFU)/ml)

|  | Subconfluent | | Confluent | |
| --- | --- | --- | --- | --- |
| Viruses | 24 hrs | 48 hrs | 24 hrs | 48 hrs |
| R8306 | $4.0 \times 10^6$ | $3.4 \times 10^6$ | $6.7 \times 10^6$ | $4.0 \times 10^6$ |
| R8308 | $5.0 \times 10^6$ | $1.0 \times 10^7$ | $2.1 \times 10^7$ | $1.4 \times 10^7$ |
| HSV-1(F) | $3.6 \times 10^7$ | $4.0 \times 10^7$ | $1.8 \times 10^7$ | $4.0 \times 10^7$ |

Figure 2:
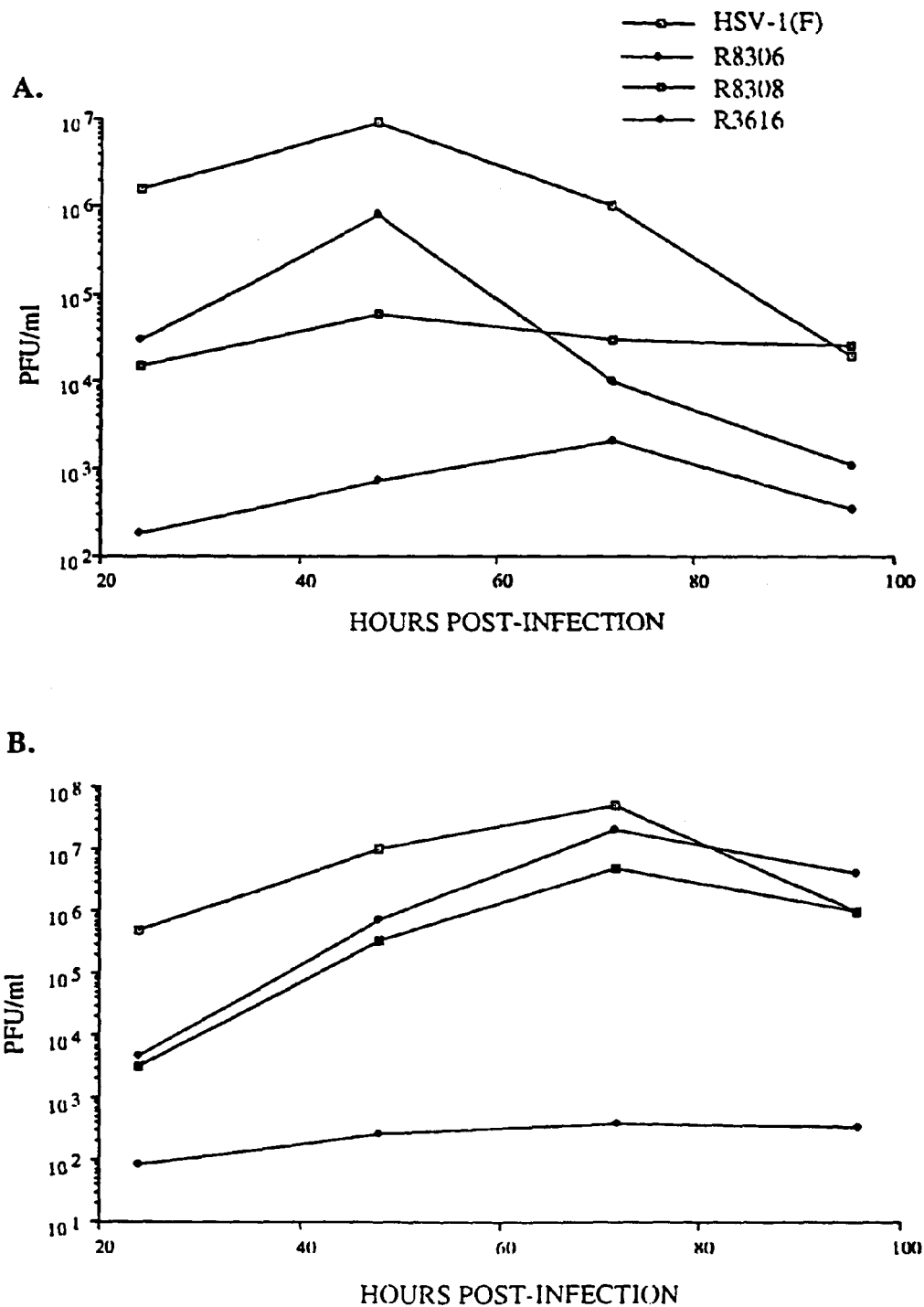
FIGS. 2A and 2B show results from replication comparison studies of wild-type [HSV-1(F)] and recombinant HSVs (R8306, R8308, and R3616) in human foreskin fibroblasts. Human foreskin fibroblast cultures were either replicating, sparse monolayers (FIG. 2A) or contact-inhibited, confluent monolayers (FIG. 2B) when infected with 0.1 PFU/cell of HSV-1 (F) (open squares), R8306 (IL-4; closed circles), R8308 (IL-10, closed squares) or R3616 (open circles). Replicate cultures were harvested at 24 hour intervals and virus titers determined.

Replication comparison studies were also conducted using dividing and non-dividing human foreskin fibroblasts. More particularly, growth comparison studies of recombinant virus (R8306, R8308, or R3616) and HSV-1(F) were conducted on dividing or contact-inhibited cultures of human foreskin fibroblasts infected at an MOI of 0.1 PFU/cell. Infected cells were harvested daily and titers were determined. As shown in FIGS. 2A and 2B, HSV-1(F) attained approximately equivalent maximum titers in dividing (FIG. 2A) or contact-inhibited (FIG. 2B) cultures at 48 or 72 hours, respectively, after infection. In contact-inhibited cultures (FIG. 2B) replication of all viruses was initially slower but by 72 hours post-infection, yields of IL-4 and IL-10-carrying-viruses were close to those of the wild-type virus.

Although the two recombinant viruses, R8306 (IL-4) and R8308 (IL-10) were constructed from a common parent virus (R3616) lacking both copies of the $\gamma_1 34.5$ gene, they replicated better than R3616 in the human foreskin fibroblast cultures. In fact, in all assays, R3616 grew poorly while R8306 and R8308 recombinant viruses grew almost as well as the wild-type virus.

Example 3

Replication of Wild-Type and Recombinant Viruses in Tumor Cell Lines

Much as set forth in Example 2, replication comparison studies were conducted with recombinant virus (R8306, R8308, or R3616) or wild-type virus [HSV-1(F)] in U251MG and D54MG human malignant glioma cells [D. D. Bigner, Duke University, Durham, N.C.]. Glioma cell lines, U251MG and D54MG, were seeded at subconfluent densities and infected with at an MOI of 1 PFU/cell with R8306, R8308, or R3616. HSV-1(F) was used as the wild-type control. After adsorption (one hr, 37° C.), monolayers were washed, overlaid with medium and further incubated (37° C., 5% $CO_2$). Cell monolayers were harvested at four 12, 24, 48 and 72 hours post-infection and were lysed by sonication. Lysates were assayed for their ability to form plaques on Vero cell monolayers as described in Example 2.

Figure 3:
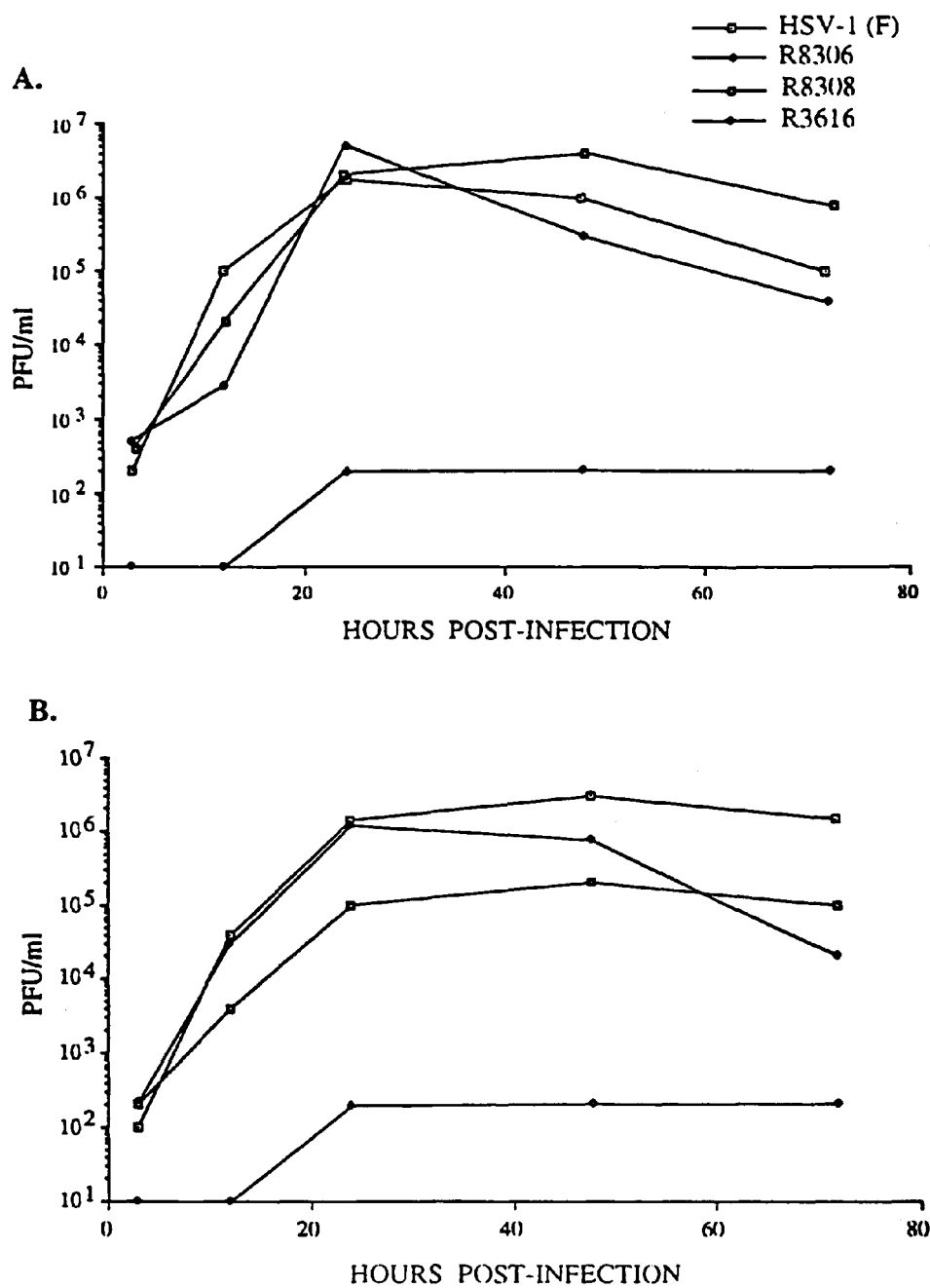
FIGS. 3A and 3B show a comparison of the replication ability of wild-type [HSV-1(F)] and recombinant HSV (R8306, R8308, or R3616) in human malignant glioma cell lines (U-251MG or D-54MG). Replicating monolayers of U-251MG (FIG. 3A) or D-54MG (FIG. 3B) human glioma cell lines were infected at 1 PFU/cell with HSV-1(F) (open squares), R8306 (closed circles) R8308 (closed squares) or R3616 (open circles). Replicate cultures were harvested for 12, 24, 48, and 72 hours post-infection, with viral titers determined on Vero monolayers.

Results, shown in FIGS. 3A and 3B, indicated that in the U251MG cells, peak titers were obtained 24 hours post-infection with which viruses, with high titers persisting for at least another 48 hours. The R8306 and R8308 recombinant viruses replicated to a level close to that of the wild-type virus, whereas the R3616 recombinant virus replicated at significantly lower levels.

In D54MG glioma cells, peak titers were obtained 48 hours post-infection, with almost identical virus titers obtained at 24 and 72 hours post-infection. R8306 and R8308 recombinant viruses grew to titers which were, at most, ten-fold lower that those of the wild-type virus whereas the titers of R3616 were significantly lower.

Example 4

Production of Cytokines by Recombinant HSV-Infected Cells

In order to quantify the amount of cytokines produced by the recombinant viruses of the invention, replicate cultures of Vero cells were either mock-infected or infected with [R8306, R8308, R3616, or HSV-1(F)] [?] at an MOI of 1.0 PFU/cell. Culture medium was collected at 48 hours post-infection, clarified by centrifugation, and the levels of cytokines were determined by enzyme-linked immunosorbent assay (ELISA) as described previously [VanCott et al., *J. Immunol.* 156:1504-1514 (1996)]. More particularly, Falcon Microtest II plates (Becton-Dickinson) were coated with 100 μl of anti-cytokine antibody diluted in PBS and incubated overnight at 4° C. Anti-cytokine antibodies used were JES6-1A12, 5.0 μg/ml (IL-2), BVD4-1D11, 2.0 μg/ml (IL-4), TRFK-5, 10.0 μg/ml (IL-5), JES5-2A5, 2.0 μg/ml (IL-10) and were obtained from PharMinigen [San Diego, Calif.]. The wells were blocked with PBS-T (phosphate buffer saline—Tween) containing 1% BSA (bovine serum albumin) at room temperature for one hour. Serial two-fold dilutions of supernates were added to duplicate wells and incubated overnight at 4° C. The wells were washed with PBS-T and incubated with appropriate biotinylated anti-cytokine mAB (monoclonal antibody) diluted in PBS-T with 1% BSA for one to two hours. The following biotin-rat anti-mouse (PharMinigen) were used: JES6-5H4, 0.4 μg/ml (IL-2), BVD4-24G2, 0.2 μg/ml (IL-4), TRFK-4, 4.0 μg/ml (IL-5) and SXC-1, 0.3 μg/ml (IL-10). After thorough washing, wells were incubated with peroxidase-labeled anti-biotin antibody (0.5>g/ml; Vector Laboratories, Burlingame, Calif.) for one hour and developed with ABTS-containing $H_2O_2$ (Moss, Inc., Pasadena, Md.). Standard curves were generated using murine rIL-2 (PharMingen), rIL-4 (Endogen, Boston, Mass.), rIL-5 and rIL-10 (Genzyme, Cambridge, Mass.). Background was determined for each cytokine assay by substituting different recombinant cytokines as the only change.

As shown in Table 2, the interleukin-carrying recombinant viruses induced the production of cytokines to levels ranging from 1,300 to 1,900-fold higher than the background amounts measured in the mock-infected cells. The background levels detected represent the lower limit of sensitivity of the respective ELISAs. As expected, cells infected with R3616 also produced only background levels of the measured cytokines.

TABLE 2

| | Expression of Cytokines in Vero Cell Infected with Recombinant Virus | | |
| --- | --- | --- | --- |
| Cytokine | Infected Cells | Mock-infected Cells* | Ratio |
| IL-4 | 40 ng | <30 pg | >1,300 |
| IL-10 | 75 ng | <39 pg | >1,900 |

*Values given represent level of sensitivity of the assay.

Example 5

Survival of C57BL/6 Mice with Intracerebral GL-261 Gliomas

While the following is exemplified in terms of gliomas, other CNS neoplastic diseases, i.e. neoplasia of neurons (e.g., neuroblastoma, ganglioneuroma), neoplasia of undifferentiated cells (e.g., medulloblastoma), neoplasia of supporting tissue (e.g., meningioma, schwannoma), and neuroplasia of metastatic origin may be successfully treated according to the invention. Further, although the following is exemplified by use of murine interleukins, interleukins from other mammals may be used to practice the invention.

To establish the sensitivity of tumor cells for the direct cytolytic effects of viruses lacking the $\gamma_1 34.5$ genes as well as viruses lacking the $\gamma_1 34.5$ genes but containing DNA encoding murine interleukins, GL-261 gliomas were induced in C57BL/6 mice and treated with the viruses. Generally, GL-261 glioma cells [purchased from Division of Cancer Treatment Tumor Repository, Fredrick, Md.; Ausman, et al., *Cancer Res.* 30:2394-2400 (1970)] were maintained in culture in Dulbecco's Modified Eagle Medium mixed 1:1 with Ham's Nutrient Mixture-F12, supplemented with 2 mM L-glutamine and 7% fetal bovine serum and needed cells were harvested from culture, washed in serum-free Dulbecco's Modified Eagle Medium mixed 1:1 with Ham's Nutrient Mixture-F12, counted in trypan blue dye to identify live cells. Prior to injection into animals, GL261 cells were diluted in an equal volume of 10% methyl cellulose to achieve doses of $10^3$, $10^4$ and $10^5$ cells/5 µl. A 5 µl aliquot was inoculated in the right caudate nucleus of the animal as described previously [Andreansky et al., *Proc. Natl. Acad. Sci., USA* 93:11313-11318 (1996)]

Delayed-therapy experiments were undertaken and animals were randomized in groups of ten. In a typical experiment, $10^5$ GL-261 cells were implanted in the right cerebral hemisphere, allowed to divide for five days before graded doses of different viruses were injected intratumorally in a volume of 5 µl. In parallel control groups, to mice received saline solution instead of virus. All tumor bearing C57BL/6 mice were followed for survival in order to establish Kaplan-Meier survival plots, (see e.g., Chambers et al., *Proc. Natl. Acad. Sci, USA* 92:1411-1415 (1995) and Andreansky et al., *Proc. Natl. Acad. Sci., USA* 93:11313-11318 (1996)]. Parallel groups of tumor-bearing mice treated similarly were randomly assigned to survival intervals of three and seven days post virus therapy, when their brains were harvested and for immunohistochemical analysis. As mice became moribund from progressive tumor growth, they were euthanized and their survival time taken as the date of euthanasia.

Figure 4:
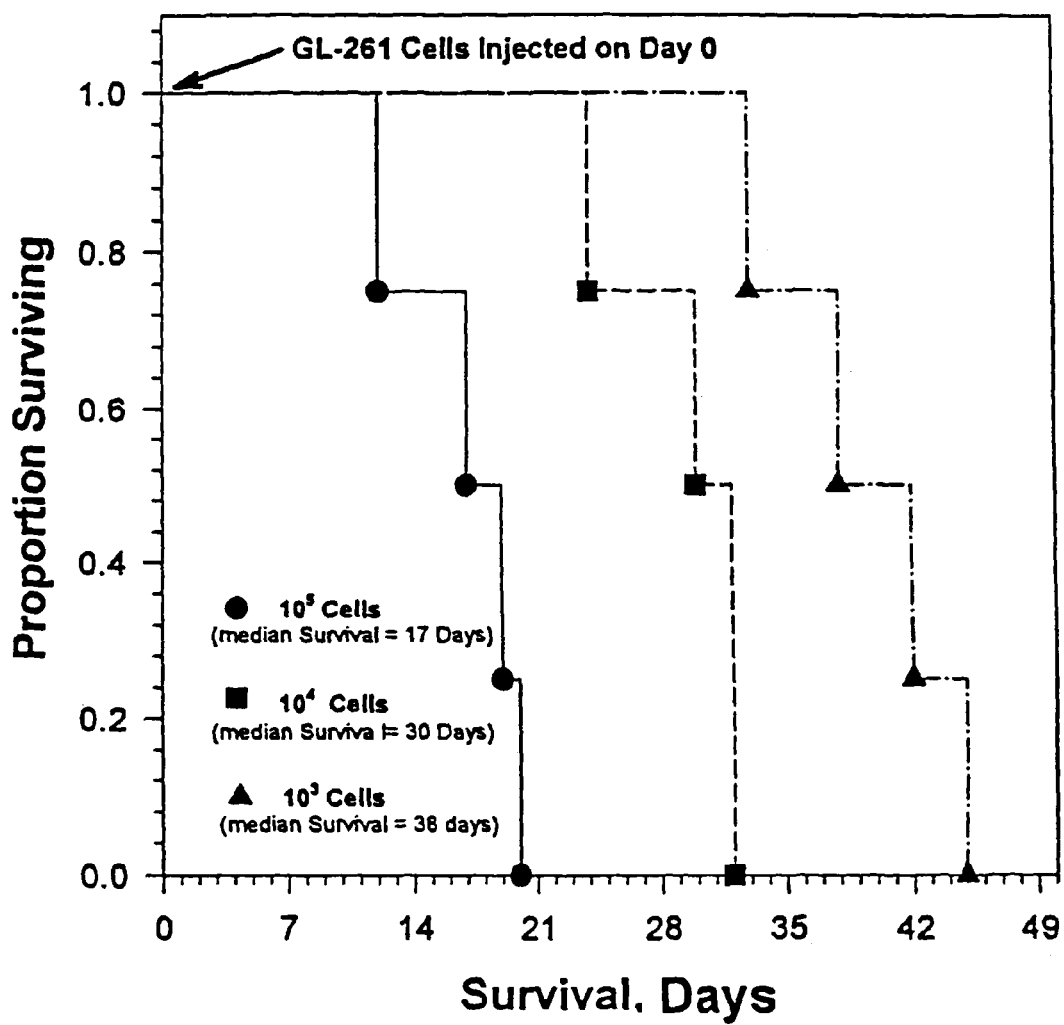
FIG. 4 shows the results of dose-response studies wherein host survival was determined after administration of GL-261 glioma cells. C57BL/6 mice were injected intracerebrally with $10^3$ (closed triangle), 104 (closed squares) or $10^5$ (closed circles) GL-261 cells suspended in 5 μl of 5% methylcellulose in DMM/F12 serum-less medium. Mice were followed until moribund and euthanized when uncharacteristically unresponsive to touch.

Preliminary studies were conducted in order to determine the relationship between the quantity of GL-261 glioma cells injected intracerebrally and host survival. Injection of $10^3$ to $10^5$ GL-261 cells into the right cerebral hemisphere of adult C57BL/6 mice resulted in a dose-dependent decrease in the median survival time (FIG. 4). In this study, mice receiving the highest dose had a median survival of 17 days, and those receiving progressively fewer tumor cells ($10^4$ or $10^3$) survived correspondingly longer (30 and 38 days median survival, respectively). These survival differences were statistically significant when the later values were compared to those of mice receiving the highest inoculum ($p<0.01$ and $p<0.0001$, respectively).

For the purposes of these glioma model studies, a dose of $10^5$ GL-261 cells was selected since this produced a median survival of 17-19 days that was reproducible and would provide a rapid answer regarding the capacity of these recombinant viruses to exert an anti-tumor effect and prolong survival.

Figure 5:
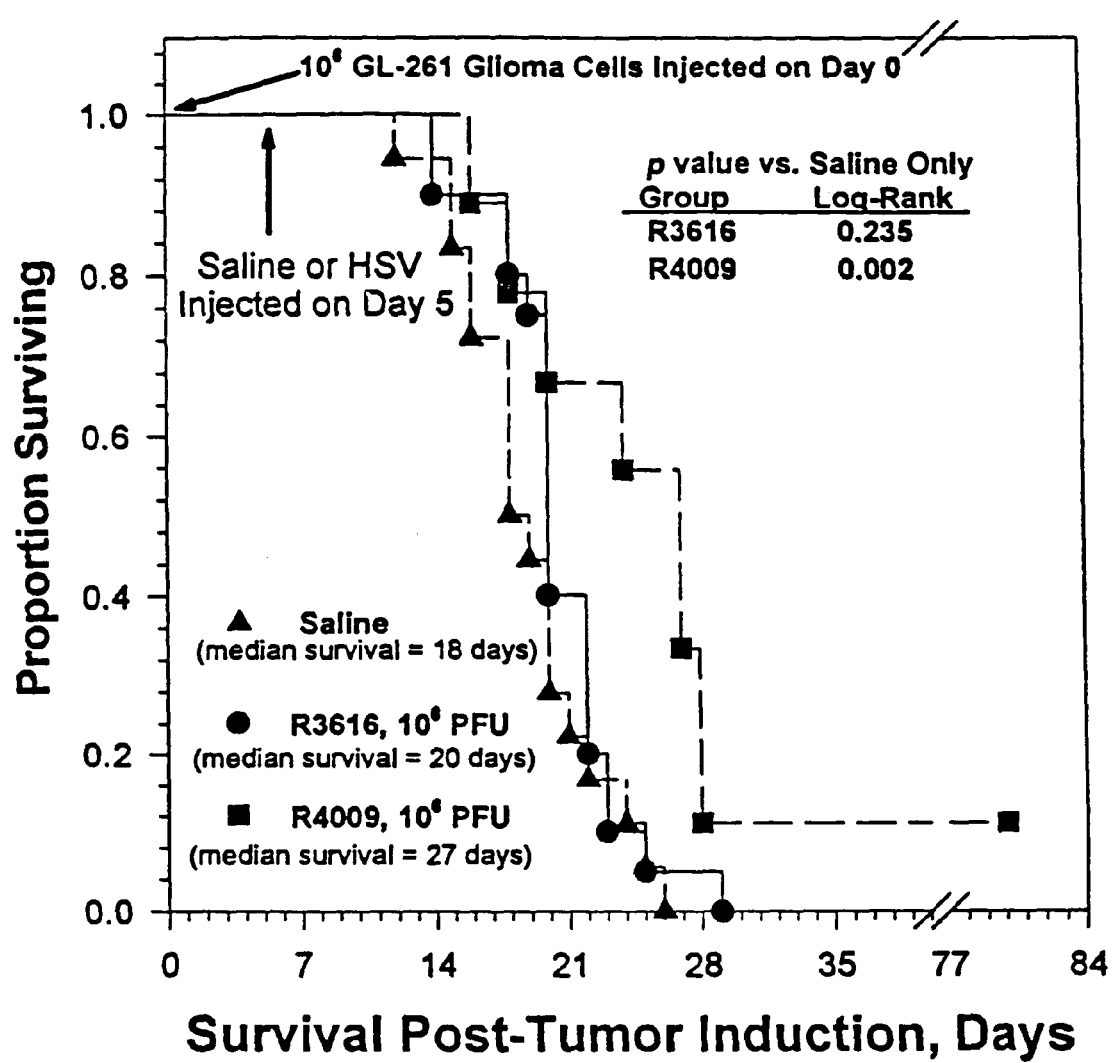
FIG. 5 shows the oncolytic effect of $\gamma_1 34.5^-$ HSV for GL-261 gliomas. C57BL/6 mice were injected intracerebrally with $10^5$ GL-261 glioma cells and five days later received a 5 μl intratumoral injection of excipient solution (closed triangles) or $10^6$ PFU of either R3616 (closed circles) or R4009 (closed squares) HSV. Mice were followed until moribund and euthanized when uncharacteristically unresponsive to touch. R4009-treated mice surviving 80 days were euthanized as long-term survivors.

Five days after injection with GL-261 cells, the mice were randomized into groups of ten animals and given an intratumoral injection of either $10^6$ PFU of R3616 or R4009 HSV or sterile excipient used to suspend the viruses (5 µl total volume). Mice receiving R3616 HSV, the parent virus from which R8306 and R8308 were constructed, had a median survival of 19 days, which was not statistically significant ($p=0.10$, log-rank) from the median survival of mice receiving the sterile excipient solution (FIG. 5). On the other hand, mice receiving R4009 had a median survival of 27 days, which was statistically longer ($p=0.0020$) than mice receiving excipient alone. This difference was similar to what has been previously reported for these two mutants using a different glioma model, the MT539MG induced and treated intracerebrally in scid mice [Chambers et al., *Proc. Natl. Acad. Sci., USA* 95:1411-1415 (1995)]

Figure 6:
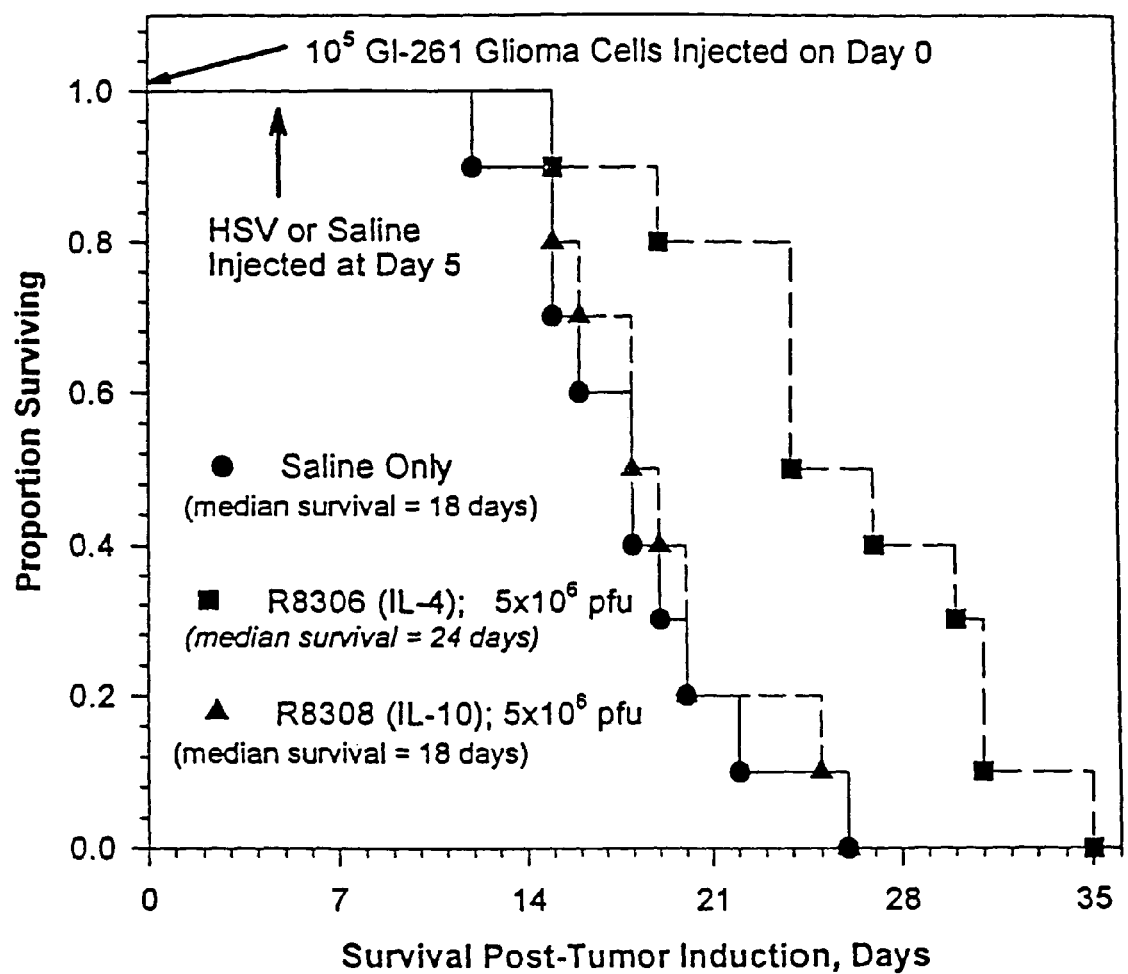
FIG. 6 shows the anti-tumor effect of $\gamma_1 34.5$ HSV containing DNA encoding cytokines for GL-261 gliomas. C57BL/6 mice were injected intracerebrally with $10^5$ GL-261 glioma cells and five days later received a 5 μl intratumoral injection of excipient solution (closed circles) or $5\times10^6$ PFU of either R8306 (closed squares) or R8308 (closed triangles). Mice were followed until moribund and euthanized when uncharacteristically unresponsive to touch.

To establish the sensitivity of GL-261 glioma cells toward HSVs lacking the $\gamma_1 34.5$ genes but that expressed murine interleukins, GL-261 glioma cells were implanted intracerebrally in C57BL/6 mice and five days post-implantation, tumor-bearing mice were injected with $5 \times 10^6$ PFU of R8306 or R8308 viruses or with sterile excipient solution through the same burr hole to the same stereotactic coordinates used to implant the tumor cells. Survival of mice in each group was monitored and results are shown in FIG. 6. Mice receiving saline experienced a predictable median survival of 18 days, while mice receiving a single dose of R8306 (IL-4) had a median survival of 24 days. This difference was statistically significant ($p=0.0016$, Log-rank) and was reproducible in several experiments. In contrast, the median survival of mice that received R8308 (IL-10) was not different from that of the mice receiving sterile excipient solution (18 days; $p=0.8585$).

Figure 7:
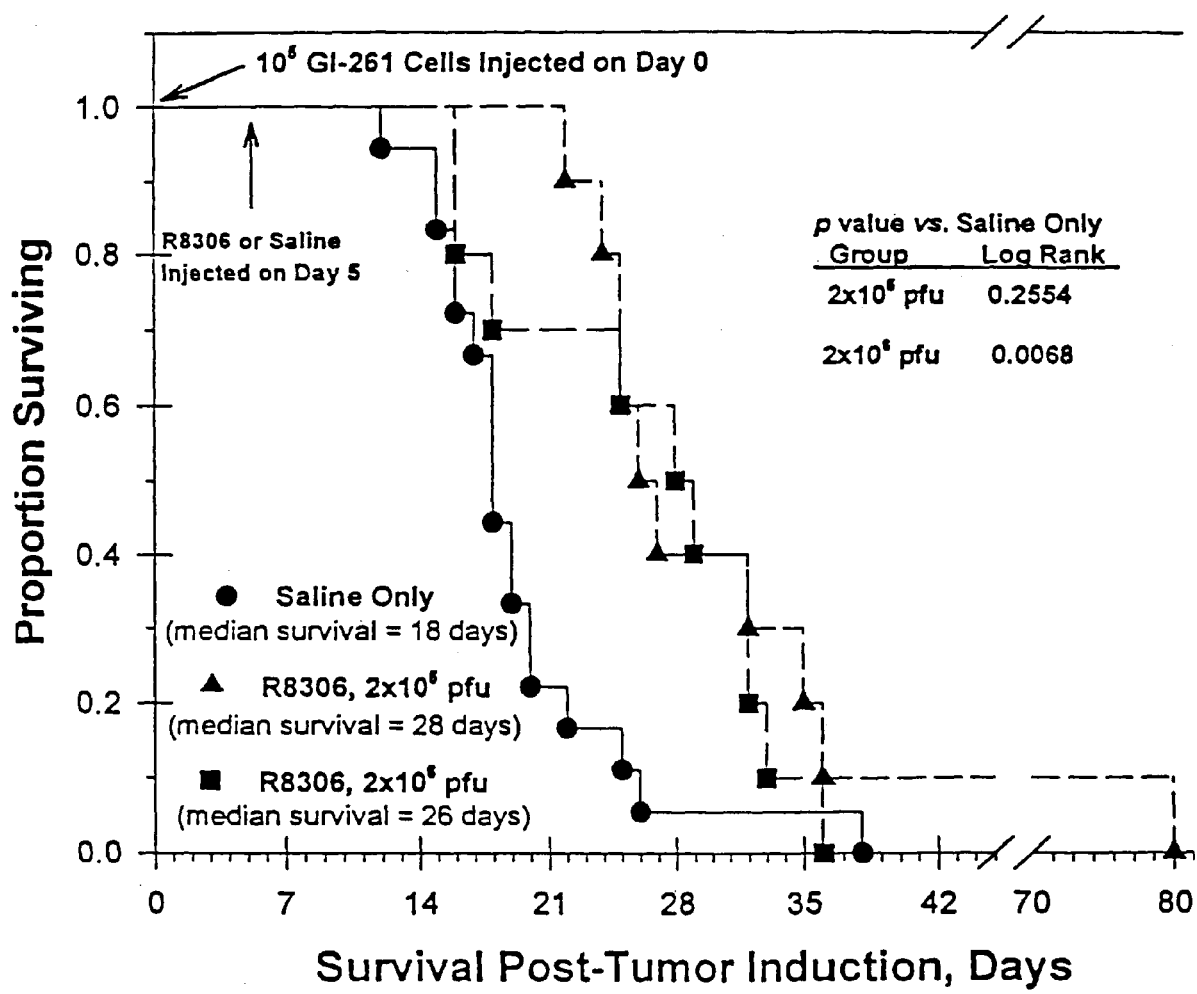
FIG. 7 shows the anti-tumor effect of $\gamma_1 34.5^-$ HSV containing DNA encoding IL-4 for GL-261 gliomas. C57BL/6 mice were injected intracerebrally with $10^5$ GL-261 glioma cells and five days post-injection received a 5 μl intratumoral injection of excipient solution (closed circles) or $2\times10^5$ PFU of R8306 (closed squares) or $2\times10^6$ PFU of R8306 (closed triangles). Mice were followed until moribund and were euthanized when uncharacteristically unresponsive to touch.

Finally, in order to determine the ability of the R8306 HSV to produce a statistically significant increase in survival, GL-261 glioma-bearing mice received either $2 \times 10^5$ PFU or $2 \times 10^6$ PFU of R8306 or sterile excipient solution five days post-tumor cell implantation. Compared with the excipient solution treated mice (results are set forth in FIG. 7), the higher dose produced a significant increase in survival ($p=0.0068$; Peto-Wilcoxon) while the lower dose did not produce a significant increase in survival ($p=0.2554$).

Example 6

Infiltration of Immune-Related Inflammatory Cells in GL-261 Gliomas

In order to assess the infiltration of immune-related inflammatory cells into tumor sites, virus-treated and saline-treated C57BL/6 mice [see Example 5; $2 \times 10^6$ PFU of R3616, R8306 or R8308 HSVs or sterile excipient solution (5 µl)], having been previously implanted with GL-261 glioma cells, were euthanized at three and seven day intervals and brains were frozen in Tissue-Tek O.C.T. compound (Miles, Kankakee, Ill.). In a separate group of mice, instead of implanting intracranial tumor cells, defined stab wounds were generated in the same location with a needle to provide a control group for mechanical trauma produced by intracerebral injection.

In all experimental groups, serial sections of brains were cut at 10-12 µm intervals and mounted on TEPSA-coated slides, fixed in 95% ethanol, and blocked in PBS-2% BSA. Endogenous peroxidase activity was blocked by incubation for 30 mins at room temperature with 0.3% $H_2O_2$ in methanol. Immunoperoxidase staining was performed using the avidin-biotin complex peroxidase Vectastain® ABC kit (Vector Laboratories, Inc., Burlingame, Calif.). Slides were incubated with primary antibodies for 30 min at room temperature. Monoclonal antibodies (Tissue Core, University of Alabama, Birmingham, Ala. USA) for inflammatory cells used were GK1.5 (CD4+), Lyt2 (CD8+), JA12.5 (IgD) and F4/80 (macrophage). Herpes simplex virus (HSV) was detected with a rabbit polyclonal antibody to HSV thymidine kinase (William Summers, Yale University, New Haven, Conn. USA). After washing thoroughly, sections were incubated with appropriate biotin-labeled secondary antibodies (Vector Laboratories, Inc., Burlingame, Calif.) for 30 mins at room temperature. Color reaction was carried out using 3,3'-diaminobenzidine according to manufacturer's instructions. Tissue sections were counterstained with Mayer's haematoxylin and permanently mounted with permount. Sections of spleen, liver, and kidney from the same animal served as the negative control. Positively staining immune-related inflammatory cells in four high power fields (400×) that included tumor cells were counted and averages determined for each cell type.

Microscopic inspection of these sections revealed that the most prevalent intratumoral immune-related cell type was the macrophage. Macrophages were the most obvious cell type three days after virus injection (8 days after tumor induction) and increased markedly by seven days post-treatment. There seemed to be little differences in the proportions of macrophages in these tumors regardless of treatment. However, it was noted that the numbers of CD8+ cells were decreased in tumors of mice treated with R8308 (IL-10).

In addition, adjacent sections tested with the HSV antibody revealed an occasional positively stained cell at day 3 but an absence of any positively stained cells by day 7 post treatment.

Sections of tissues (spleen, liver, kidney) from these same mice were used as positive controls for the anti-leukocyte antibodies. No discernible differences were noted in the distribution or staining patterns of these tissues as a result of recombinant virus injection into the brains of these mice (not shown). These tissues were also negative for HSV by antibody staining.

The data obtained from the studies herein and set forth above indicate that:

(1) as in the scid mice implanted with either murine or human glioma cells, the C57BL/6 mouse proved suitable for intracranial induction of tumors that were uniformly fatal;

(2) an inoculum of $10^5$ tumor cells yielded reproducible tumor development with a median mortality in a reasonable period of time to permit post tumor induction therapies, i.e., slightly longer than two weeks;

(3) genetically-engineered HSV recombinants allowed for efficient expression of the cytokine genes inserted into the viral genomes;

(4) survival of neoplastic disease-bearing mice treated with recombinant viruses varied depending on the cytokine gene inserted into the virus; and (5) overall, these studies provide evidence that host immunity to cells of CNS neoplastic disease played a role in the oncolytic effects achieved by viral treatment of tumors with replication competent, attenuated cytotoxic viruses.

The data also provide evidence that regulation of the immune response, indeed, does contribute to survival from CNS neoplastic diseases. More specifically, the HSV/IL-4 recombinant virus prolonged survival and was associated with striking infiltration of the tumor by macrophages, CD4+ and CD8+ T cells. In contrast, the HSV/IL-10 recombinant virus, which down-regulates the immune response, led to survival rates that were no different than those seen with HSV R3616 or saline-treated controls.

The foregoing detailed description is given for clearness of understanding only, and no unnecessary limitations should be understood therefrom, as modifications within the scope of the invention will become apparent to those skilled in the art.

What is claimed is:

1. A recombinant herpes simplex virus that preferentially kills tumor cells and not healthy cells, that expresses only one $\gamma_1 34.5$ gene copy and that comprises an expressible tumor-growth-inhibiting cytokine-encoding DNA.

2. The recombinant herpes simplex virus of claim 1 wherein said virus lacks all or part of a $\gamma_1 34.5$ gene copy.

3. The recombinant herpes simplex virus of claim 2 wherein said virus comprises a $\gamma_1 34.5$ gene having a deletion of a portion of a coding sequence of said $\gamma_1 34.5$ gene, said deletion comprising a Bst EII-Stu I fragment of said $\gamma_1 34.5$ gene.

4. The recombinant herpes simplex virus of claim 1 wherein said virus comprises a $\gamma_1 34.5$ gene having a stop codon at a Bst EII site in said $\gamma_1 34.5$ gene.

5. The recombinant herpes simplex virus of claim 1 wherein said expressible tumor-growth-inhibiting cytokine-encoding DNA is under the promoter-regulatory control of a herpes simplex virus gene promoter.

6. The recombinant herpes simplex virus of claim 5 wherein said herpes simplex virus gene promoter is an EGR-1 promoter.

7. The recombinant herpes simplex virus of claim 1 wherein said tumor-growth-inhibiting cytokine-encoding DNA is under the promoter-regulatory control of a synthetic herpes simplex virus-derived promoter.

8. The recombinant herpes simplex virus of claim 7 wherein said synthetic herpes simplex virus-derived promoter comprises a herpes simplex virus α gene promoter fragment operatively linked 5' to a herpes simplex virus γ gene promoter fragment.

9. The recombinant herpes simplex virus of claim 8 wherein said α gene promoter fragment comprises promoter sequences upstream of the transcription initiation site of the α4 gene and said γ gene promoter fragment comprises a transcription initiation site and the 5' transcribed non-coding sequence of the $\gamma_1 U_L 9$ gene.

10. The recombinant herpes simplex virus of claim 1 wherein an unexpressed $\gamma_1 34.5$ gene copy is replaced by said expressible tumor-growth-inhibiting cytokine-encoding DNA.

11. The recombinant herpes simplex virus of claim 1 wherein said virus comprises two or more copies of said tumor-growth-inhibiting cytokine-encoding DNA.

12. The recombinant herpes simplex virus of claim 10 where said herpes simplex virus is a HSV-1.

13. The recombinant virus of claim 1 wherein said tumor-growth-inhibiting cytokine-encoding DNA further comprises a polyadenylation signal.

14. The recombinant virus of claim 13 wherein said polyadenylation signal is a hepatitis B virus-derived polyadenylation signal.

15. A method for treating neoplastic disease, the method comprising administering to a target tumor, a recombinant herpes simplex virus capable of expressing only one $\gamma_1 34.5$ gene copy and comprising an expressible tumor-growth-inhibiting cytokine-encoding DNA, wherein the expressed cytokine augments tumor cell killing.

16. The method of claim 15 wherein said recombinant herpes simplex virus lacks all or part of an unexpressed $\gamma_1 34.5$ gene copy.

17. The method of claim 15 wherein said recombinant herpes simplex virus comprises a $\gamma_1 34.5$ gene having a stop codon at a Bst EII site in said $\gamma_1 34.5$ gene.

18. The method of claim 15 wherein said recombinant herpes simplex virus comprises a $\gamma_1 34.5$ gene lacking a portion of the coding sequence corresponding to a Bst EII/Stu I restriction fragment of said $\gamma_1 34.5$ gene.

19. The method of claim 15 wherein said expressible tumor-growth-inhibiting cytokine-encoding DNA is under the promoter-regulatory control of a herpes simplex virus gene promoter.

20. The method of claim 19 wherein said herpes simplex virus promoter is an EGR-1 promoter.

21. The method of claim 15 wherein said tumor-growth-inhibiting cytokine-encoding DNA is under the promoter regulatory control of a synthetic herpes simplex virus-derived promoter.

22. The method of claim 21 wherein said synthetic herpes simplex virus-derived promoter comprises a herpes simplex virus α gene fragment operatively linked 5' to a herpes simplex virus γ gene promoter fragment.

23. The method of claim 22 wherein said α gene promoter fragment comprises a promoter sequence upstream of the transcription initiation site of said α gene promoter fragment comprising the transcription initiation site and the 5' transcribed non-coding sequence of the $U_L 19$ gene.

24. The method of claim 15 wherein said $\gamma_1 34.5$ gene is replaced by said expressible tumor-growth-inhibiting cytokine-encoding DNA.

25. A pharmaceutical composition comprising in a pharmaceutically acceptable carrier, diluent, or adjuvant, a recombinant herpes simplex virus expressing only one $\gamma_1 34.5$ gene copy, said virus comprising an expressible tumor-growth-inhibiting cytokine-encoding DNA, wherein the expressed cytokine augments tumor cell killing.

26. The method of claim 15, wherein the target tumor is a tumor of the central nervous system.

27. The recombinant herpes simplex virus of claim 3, wherein the expressible tumor growth inhibiting cytokine-encoding DNA is selected from DNA encoding IL-1, IL-2, IL-A, IL-6, IL-7, IFN-γ, GM-CSF or TNF-α.

28. The method of claim 15, wherein the expressible tumor growth inhibiting cytokine-encoding DNA is selected from DNA encoding IL-1, IL-2, IL-4, IL-6, IL-7, IFN-γ, GM-CSF or TNF-α.

* * * * *